United States Patent [19]
Barthel et al.

[11] Patent Number: 5,941,816
[45] Date of Patent: Aug. 24, 1999

[54] VIEWING SYSTEM WITH ADAPTER HANDLE FOR MEDICAL BREATHING TUBES

[75] Inventors: Thomas C. Barthel, Becker, Minn.; Alan H. Shikani, Baltimore, Md.; Mark F. Brown, Coon Rapids; George A. Klemmer, Minneapolis, both of Minn.

[73] Assignee: Clarus Medical Systems, Inc., Minneapolis, Minn.

[21] Appl. No.: 08/834,266

[22] Filed: Apr. 15, 1997

[51] Int. Cl.$^6$ ........................................................ A61B 1/00
[52] U.S. Cl. .............................................. 600/120; 600/194
[58] Field of Search ..................................... 600/120, 131, 600/188, 194; 128/200.26, 207.14, 207.15

[56] References Cited

U.S. PATENT DOCUMENTS

| | | | |
|---|---|---|---|
| 3,677,262 | 7/1972 | Zukowski | 128/6 |
| 3,776,222 | 12/1973 | Smiddy | 128/6 |
| 4,126,127 | 11/1978 | May | 128/6 |
| 4,319,563 | 3/1982 | Kubota | 128/6 |
| 4,561,446 | 12/1985 | Hetz | 128/660 |
| 4,782,819 | 11/1988 | Adair | 128/6 |
| 4,798,193 | 1/1989 | Giesy et al. | 128/7 |
| 4,800,870 | 1/1989 | Reid, Jr. | 128/6 |
| 4,846,153 | 7/1989 | Berci | 128/6 |
| 4,869,238 | 9/1989 | Opie et al. | 128/6 |
| 4,946,442 | 8/1990 | Sanagi | 604/164 |
| 4,947,896 | 8/1990 | Bartlett | 128/11 |
| 4,982,729 | 1/1991 | Wu | 128/11 |
| 5,127,393 | 7/1992 | McFarlin et al. | 128/4 |
| 5,174,283 | 12/1992 | Parker | 600/120 X |
| 5,183,031 | 2/1993 | Rossoff | 128/6 |
| 5,329,940 | 7/1994 | Adair | 128/200.26 |
| 5,337,735 | 8/1994 | Salerno | 128/11 |
| 5,400,771 | 3/1995 | Pirak et al. | 600/120 X |
| 5,431,152 | 7/1995 | Flam et al. | 600/120 |
| 5,512,034 | 4/1996 | Finn et al. | 600/138 |
| 5,551,946 | 9/1996 | Bullard | 600/120 X |
| 5,569,159 | 10/1996 | Anderson et al. | 600/114 |
| 5,636,625 | 6/1997 | Miyagi et al. | 128/200.26 |
| 5,645,519 | 7/1997 | Lee et al. | 600/120 X |

*Primary Examiner*—Beverly M. Flanagan
*Attorney, Agent, or Firm*—Olson & Hierl, Ltd.

[57] ABSTRACT

A viewing system for use with a breathing tube such as an endotracheal intubation tube or a tracheostomy tube and a viewing assembly having a viewing conduit for indirectly viewing the tracheal area of a patient into which the breathing tube is being inserted and for guiding the tube into place within the patient's trachea is disclosed. The viewing system also incorporates an adapter handle which allows the viewing assembly to be used with breathing tubes of varied lengths.

43 Claims, 6 Drawing Sheets

VIEWING SYSTEM WITH ADAPTER HANDLE FOR MEDICAL BREATHING TUBES

FIELD OF THE INVENTION

The present invention relates generally to a viewing system for assisting in endotracheal intubation or tracheostomy procedures.

BACKGROUND OF THE INVENTION

Endotracheal intubation is a very common medical procedure by which a flexible plastic endotracheal breathing tube is inserted into a patient's trachea for providing oxygen or anesthetic gases to the lungs. Usually, the endotracheal tube is introduced into the patient's trachea after the patient has been sedated or has become unconscious. Typically, the patient is placed on his or her back, and the patient's chin is lifted in order to place the patient in the so-called "sniffing" position. When the head and neck of the patient are situated to achieve the proper position, the patient's tongue typically falls downward toward the roof of the patient's mouth. The endotracheal tube must be inserted past the patient's teeth and tongue and further past the epiglottis and vocal cords into the trachea. After the endotracheal tube is advanced past the vocal cords and into the patient's trachea, the distal end of the tube should be approximately 2 to 4 centimeters (about 1 to 2 inches) in front of the bifurcation of the trachea in order to ventilate both of the patient's lungs equally.

A tracheostomy is another procedure by which a breathing tube is placed into a patient's trachea for providing oxygen or anesthetic gases to the lungs. An incision is made in the base of the patient's neck above the sternum so that a tracheostomy tube can be inserted into the patient's trachea.

In addition to proper initial placement of a breathing tube, which very often is done under emergency conditions, it is desirable to change a patient's endotracheal or tracheostomy tube approximately weekly to prevent harmful reaction from long-term intubation such as granulation tissue reaction, infection, or stenosis of the trachea, larynx, or subglottis.

In some cases, the placement of the tube is made difficult due to trauma or physical differences in the tracheal areas of different patients. Patients differ in size, age, and sex. In some cases, incorrect placement of the breathing tube may injure the patient. The tube must be placed so that it can deliver oxygen or anesthetic gas to both lungs. Serious complications may result if the tube is placed incorrectly, such as into the esophagus or into only one bronchus. With an endoscopic intubation assist device, the practitioner can view the patient's tracheal area and is able to more accurately place the tube. Existing devices, however, are not adjustable for different size patients that require various sizes of endotracheal or tracheotomy tubes.

One attempt to solve that problem is a device commonly referred to as a "laryngoscope" which is often used to move and hold the patient's tongue to permit viewing of the throat and tracheal area of the patient. Examples of laryngoscopes are disclosed in Bartlett, U.S. Pat. No. 4,947,896 entitled "Laryngoscope," and in May, U.S. Pat. No. 4,126,127, entitled "Suctioning/Oxygenating Laryngoscope Blade." A laryngoscope that incorporates fiber optics for viewing and illuminating the region around the patient's larynx is disclosed in Wu, U.S. Pat. No. 4,982,729 entitled "Rigid Fiberoptic Intubating Laryngoscope."

The common laryngoscope is somewhat of a misnomer as it is actually a combination tongue depressor and flashlight. It does not actually provide an endoscopic view of the internal anatomy. The laryngoscope is used to facilitate endotracheal intubation by forming a passageway past the patient's tongue and teeth so that the endotracheal tube can be inserted into the trachea. The practitioner must still rely on tactile feel and experience to make certain that the tube is correctly placed.

Another device that is used to assist intubation is an elongated wire or stylet made of malleable material which can be bent or shaped to accommodate a particular patient. The malleable stylet is inserted into the endotracheal tube and then used to guide the tube into place within the patient's tracheal passage. The stylet is then removed, and the tube is connected to a supply conduit which then supplies the oxygen or other gas to the lungs of the patient. In the normal practice of endotracheal intubation procedures, the medical practitioner pre-shapes a 3 to 4 mm outside diameter aluminum stylet over which the endotracheal tube is placed and then follows a blind approach to accomplish intubation.

More recent devices, however, have incorporated fiber optics to provide an endoscopic view of the tracheal area into which an endotracheal tube is to be inserted. The fiber optics are usually incorporated into the stylet which is used to guide the tube into place. Examples of intubation assist devices which incorporate fiber optics are disclosed in Adair, U.S. Pat. No. 5,329,940 entitled "Endotracheal Tube Intubation Assist Device;" Salerno, U.S. Pat. No. 5,337,735 entitled "Fiber-Lighted Stylet;" Berci, U.S. Pat. No. 4,846,153 entitled "Intubating Video Endoscope;" and Zukowski, U.S. Pat. No. 3,677,262 entitled "Surgical Instrument Illuminating Endotracheal Tube Inserter."

While these devices provide some viewing, they can be used with an endotracheal tube of only one length or a limited range of lengths within a particular category such as pediatric or adult. Also, many of these devices are relatively complicated in that they may include a suction port, oxygen or gas supplying means, gas flow directed means, or other control systems.

Other prior art devices are simply a handle with a light source from which extends an encased malleable fiber-optic cable which transmits light to the local area to be viewed. These devices resemble a flashlight with a fiber-optic cable at the end that carries light into the trachea of a patient in order to illuminate the area into which an intubation tube is to be placed. These devices, however, do not transmit an image and are of a fixed length.

Still other devices are simply a rigid tube within which is carried a fiber-optic cable and onto which is sleeved the endotracheal tube to be inserted into the patient. These do not provide a way to adjust for endotracheal tubes of varying lengths or even to adjust for differences in the size or anatomy of the patient.

The prior art patents described all disclose fixed length endoscopes that can only be used with endotracheal tubes of only one length or of a limited range of lengths. These devices necessitate different versions for the many available endotracheal tubes from pediatric to adult sizes. Also, prior art devices that use fiber optics are relatively expensive and complex and therefore are not used very often because of the high cost of operating and maintaining these devices. The cost of repairing or replacing one of these units is very high compared to that of the present invention.

A need exists in the art for an intubation assist device that allows the medical practitioner to view the tracheal area during the procedure. It would also be beneficial to be able to use one size of endoscopic viewing system with several sizes of endotracheal tubes such as from pediatric to adult sizes. The device also should be simple, inexpensive, and easy to use. The present invention meets these desires.

SUMMARY OF THE INVENTION

The present invention relates to a viewing system for use with a breathing tube to assist in endotracheal intubation or tracheostomy procedures. The viewing system includes a viewing assembly having a shaft that carries a viewing conduit such as a fiber-optic bundle. The present invention also includes an adapter handle to allow the use of varied lengths of endotracheal or tracheostomy tubes such as from pediatric to adult sizes with the shaft of the viewing assembly being a standard length. The adapter handle releasably fixes the viewing assembly within the breathing tube at the location desired by the practitioner to conform to different lengths of breathing tubes.

The invention provides an image of the endotracheal area for use as a guide during the intubation procedure. The viewing assembly provides the image via the viewing conduit carried by the elongated shaft. Also, the viewing system of the invention may be used with any length of breathing tube.

The breathing tube with which the present invention is used has proximal and distal ends and defines a lumen between the ends. The proximal end has a first mounting element which is connected to a supply of oxygen or anesthetic gas during use. The first mounting element is a standard size on all endotracheal and tracheostomy tubes, but the length of the tube may vary for different size patients such as pediatric or adult. While the breathing tube is made of flexible plastic, the first mounting element is typically made of a rigid plastic material and may be of the type commonly known as a "Luer fitting." The tube including the first mounting element is sterile. The tube may also include an inflatable cuff located near the distal end which serves to provide a seal in the trachea when inflated. The distal end of the tube is the end which is inserted into the trachea of the patient.

The viewing assembly of the present invention includes the shaft which carries the viewing conduit. The shaft has a proximal end and a distal end. In the preferred embodiment, the distal end is placed into the breathing tube and is generally aligned with the distal end of the tube. Preferably, the shaft is approximately as long as the longest available endotracheal or tracheostomy tube. In the preferred embodiment, the shaft is malleable and is made of aluminum tubing so that it can be bent or shaped to accommodate a particular patient's anatomy. The malleable shaft will substantially retain its shape in typical use once it is bent. In another preferred embodiment, the shaft is tubular so that the viewing conduit may be carried within the shaft.

The viewing conduit includes a coupling that can be connected to an image viewing apparatus. The image viewing apparatus is preferably a video monitor, but it may be a mechanical lens or other device that allows the practitioner to view the image provided by the viewing assembly. A fiber-optic bundle is the preferred viewing conduit. Also, the viewing conduit may include optic fibers which carry illumination to the end of the shaft to illuminate the endotracheal area of the patient so that the practitioner can more easily see the area into which the breathing tube is being guided. Illumination may be provided by a light source attached to the viewing conduit by a separate coupling.

The adapter handle allows the distal end of the shaft to be precisely located as desired with respect to the distal end of the breathing tube so that the image of the tracheal area can be provided. The viewing assembly and adapter handle also serve as a handle to physically guide the tube into the trachea of the patient. The advantage provided by the adapter handle of the present invention is that the shaft of the viewing assembly can be of a standard length and still be used with a breathing tube of any length.

The adapter handle is preferably a one-piece construction that allows the practitioner to securely mount the breathing tube to the viewing assembly. The adapter handle has a second mounting element which is adapted to cooperate with the first mounting element of the breathing tube to hold the shaft in place within the lumen of the tube when the first and second mounting elements are operably associated. Once the distal end of the shaft is located with respect to the distal end of the tube, the shaft is locked into place by inserting the second mounting element of the adapter handle into the first mounting element of the tube.

In one preferred embodiment, the adapter handle is an elongated hollow body defining a channel between its ends. The shaft is inserted through the channel of the adapter handle. The adapter handle preferably includes a tapered locking section for mounting within the first mounting element of the breathing tube. As the locking section is mounted, the first mounting element compresses it., The locking section in turn presses against the viewing assembly shaft which is within the adapter handle. The shaft is held in place within the tube, and the adapter handle may by used as a handle during the intubation procedure or tracheostomy.

While endotracheal and tracheostomy tubes are generally used only once, an advantage of the present invention is that the adapter handle and the viewing assembly can be reusable. Other advantages of the present invention are the relatively inexpensive and simple constructions of the adapter handle and the viewing assembly compared to prior art devices.

In accordance with the method of the present invention, the viewing system is assembled by inserting the shaft of the viewing assembly into the adapter handle and also through the breathing tube. The practitioner then aligns the distal end of the shaft of the viewing assembly with respect to the distal end of the tube. Once the viewing assembly is aligned, the adapter handle with the viewing assembly is mounted to the tube by mating the first and second mounting elements.

When mounted to the tube, the adapter handle compresses on the shaft of the viewing assembly to hold it in the desired position within the breathing tube. The adjustability provided by the adapter handle is advantageous, because the end of the viewing assembly's shaft can be placed substantially coterminously with the end of the tube. This is desirable, because the system will provide an image of the tracheal area from the point of view of the end of the breathing tube.

Another advantage of the present invention is that the locking stop and the viewing assembly, once mounted onto the tube, can be used as a handle to physically maneuver the tube past the patient's teeth, tongue, epiglottis, and vocal cords into the trachea.

When the viewing assembly and breathing tube are successfully guided to the desired position within the trachea, the adapter handle is disengaged from the tube, and the viewing assembly is removed while the tube is held in place. The cuff is then inflated and oxygen or other gases can be supplied to the patient.

Numerous other advantages and features of the present invention will become readily apparent to those skilled in the art from the following detailed description of the preferred embodiment of the invention, the drawings, and the appended claims.

DETAILED DESCRIPTION OF THE PREFERRED EMBODIMENTS

While this invention can be embodied in many different forms, there are shown in the drawings and described in detail, preferred embodiments of the invention. The present disclosure is an exemplification of the principals of the invention and is not intended to limit the invention to the embodiments illustrated.

Figure 1:
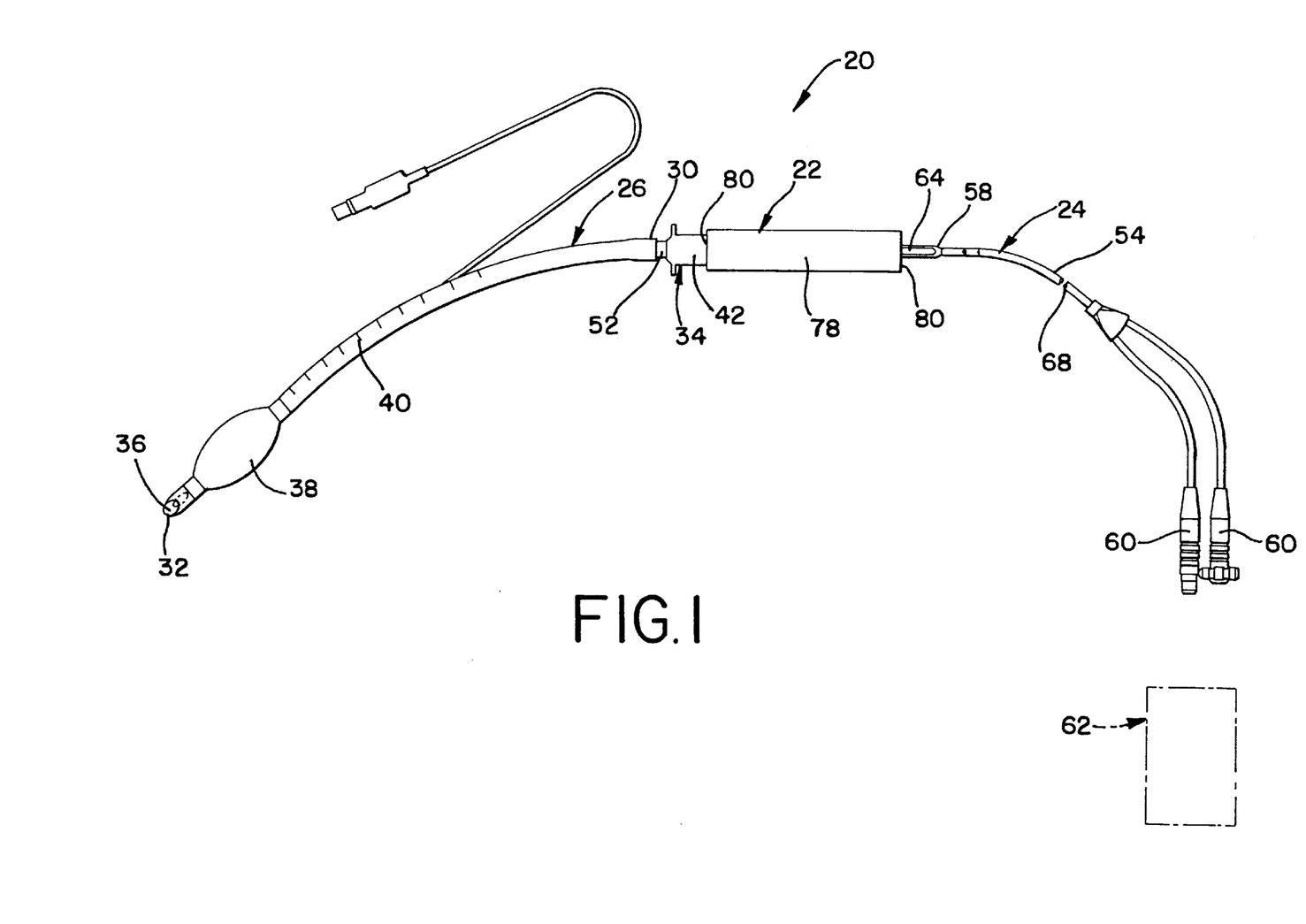
FIG. 1 is a plan view showing a viewing system of the present invention with an adapter handle and viewing assembly mounted onto an endotracheal breathing tube.
Figure 2:
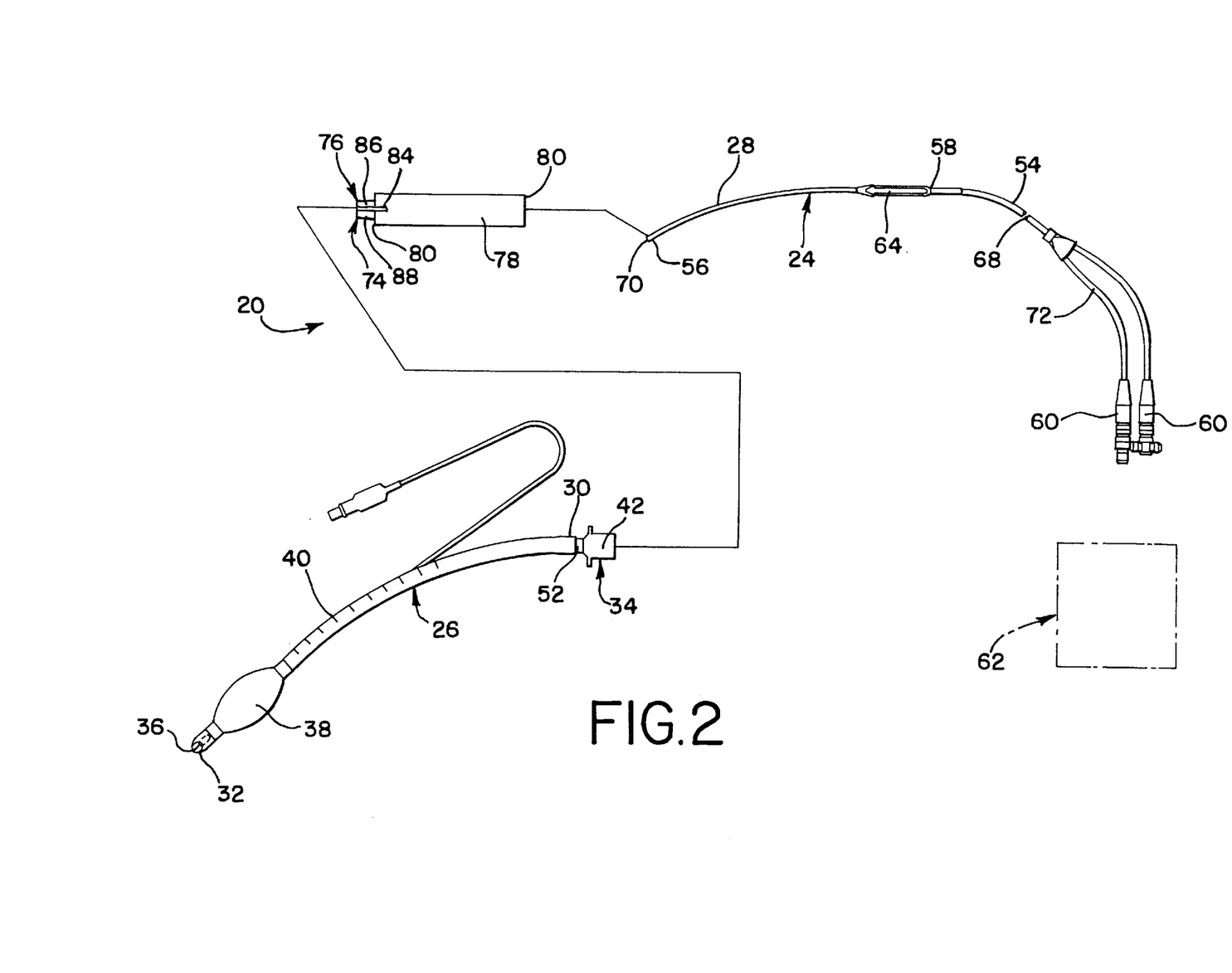
FIG. 2 is a side elevational exploded view of the viewing system of FIG. 1 showing the endotracheal tube, the adapter handle, and the viewing assembly all separated.

Referring to FIGS. 1 and 2 of the drawings, one embodiment of the present invention, a viewing system 20 with an adapter handle 22, is shown. The viewing system 20 includes a viewing assembly 24 and the adapter handle 22. The viewing assembly 24 and adapter handle 22 are used with a breathing tube such as an endotracheal tube 26. The viewing system 20, comprising the viewing assembly 24 and adapter handle 22, allows the practitioner to accomplish an endotracheal intubation procedure with the advantage of being able to see an image of the tracheal area while inserting the endotracheal tube 26. This is a vast improvement over blind intubation. It is also a great improvement over the simple laryngoscope devices of the prior art which merely illuminate but do not provide an image of the tracheal area. Also, the adapter handle 22 provides an advantage over prior art devices which incorporate fiber-optics but do not allow the use of a standard length shaft 28 with endotracheal tubes 26 of varied lengths.

The present invention may be used with any endotracheal tube 26 that is commonly available. The common endotracheal tube 26 has a proximal end 30, a distal end 32, and a first mounting element 34 on the proximal end 30, and is made of flexible plastic. The first mounting element 34 is commonly known as a "port" or "fitting." The endotracheal tube 26 also defines a lumen 36 between the ends. It is the distal end 32 of the endotracheal tube 26 that is inserted into the trachea of a patient. An inflatable cuff 38 is provided near the distal end 32 of the endotracheal tube 26. The cuff 38 is inflated after the tube 26 is in place within the trachea. Once inflated, the cuff 38 provides a seal between the tracheal wall and the endotracheal tube 26. The endotracheal tube 26 is open at both ends to allow oxygen or anesthetic gas to flow through the tube 26 and into the patient's lungs once the tube 26 is inserted into the trachea and connected to an oxygen or gas supply. A radiopaque stripe 40 may also be provided within the tube 26 so that the position of the tube 26 within the patient's trachea may be seen in an X-ray photograph.

Markings 42 along the length of the tube 26 serve to indicate how far into a patient's trachea the tube 26 is inserted. These markings 42, however, only indicate how far the distal end 32 of the tube 26 is past the patient's teeth. The location of the distal end 32 of the tube 26 with respect to the patient's bronchi is important for proper intubation. The present invention helps to locate the tube 26 accurately within the patient's trachea by providing an image of the endotracheal area during the intubation procedure.

Figure 3:
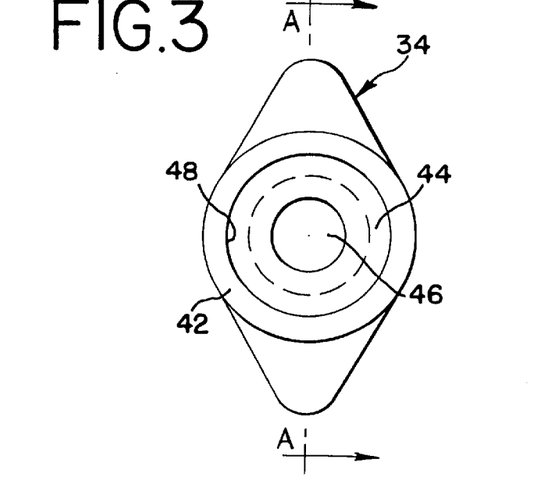
FIG. 3 is a front elevational view of the first mounting element.
Figure 4:
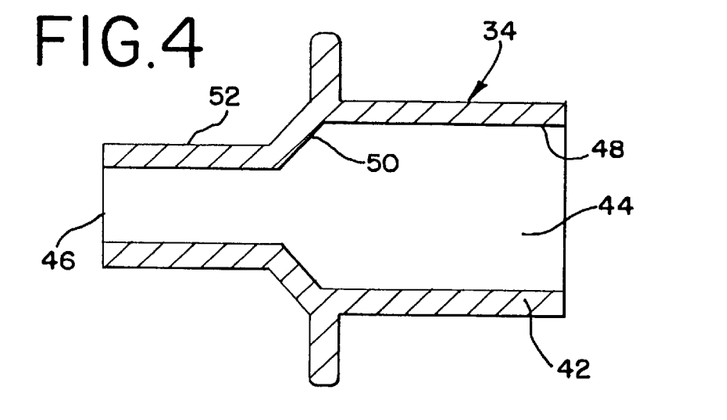
FIG. 4 is a cross-sectional view of the first mounting element taken along plane A—A of FIG. 3.
Figure 5:
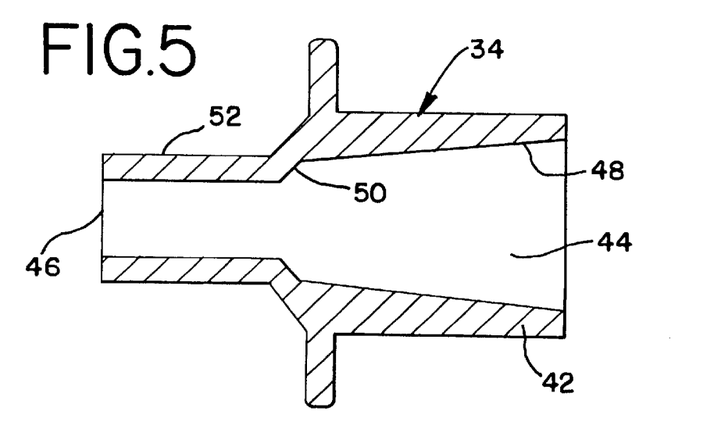
FIG. 5 is a cross-sectional view of an alternate embodiment of the first mounting element taken along plane A—A of FIG. 3.
Figure 6:
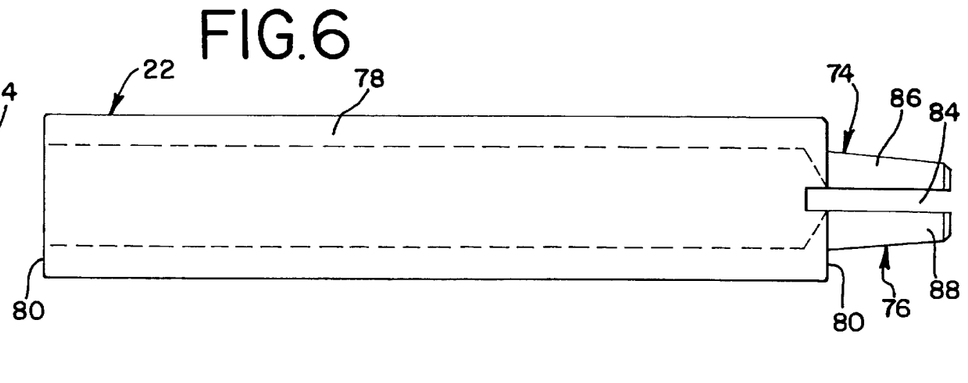
FIG. 6 is a side elevational view of the adapter handle.
Figure 7:
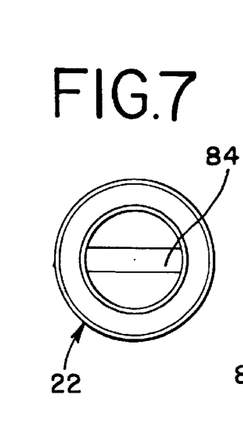
FIG. 7 is a rear elevational view of the adapter handle.
Figure 8:
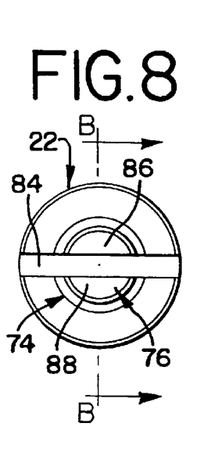
FIG. 8 is a front elevational view of the adapter handle.
Figure 9:
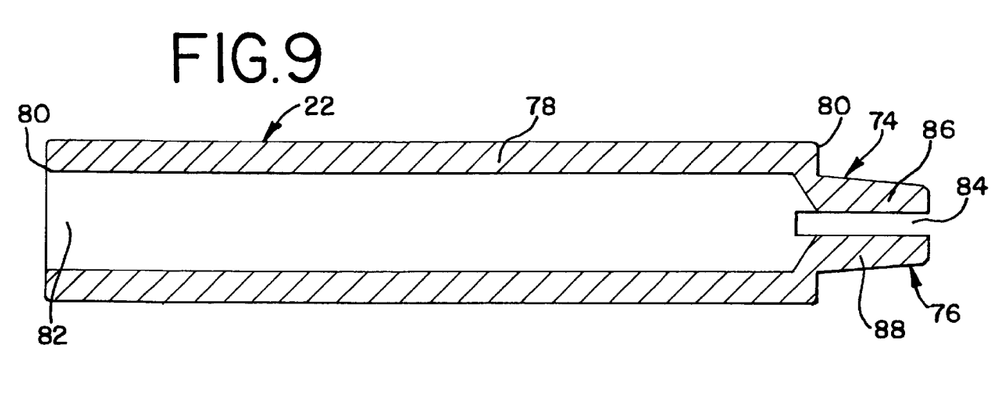
FIG. 9 is a cross-sectional view of the adapter handle taken along plane B—B of FIG. 8.

The commonly available endotracheal tube 26 is normally supplied with the first mounting element 34 on the proximal end 30. As shown in FIGS. 3 and 4, the first mounting element 34 is comprised of a hollow cylinder 42 that defines a cavity 44 having a bottom surface 50 and a hole 46 that axially cooperates with the lumen 36 of the endotracheal tube 26 to join the cavity 44 and the lumen 36. The cavity 44 of the first mounting element 34 is usually defined by a substantially cylindrical inner surface 48. An alternate embodiment, shown in FIG. 5, provides the cavity 44 with a tapered inner surface 48 such that the taper becomes narrower toward the bottom surface 50 of the cavity 44.

The first mounting element 34 may be attached to the endotracheal tube 26 in any manner that provides a seal between the endotracheal tube 26 and the first mounting element 34. In the common configuration, the endotracheal tube 26 is slipped tightly over a tubular protrusion 52 that is opposite the cavity 44. The tubular protrusion 52 has an outer diameter dimensioned to be larger than the inner diameter of the endotracheal tube 26 so that the endotracheal tube 26 fits tightly over the protrusion 52.

Other possible configurations of the first mounting element 34 may include a threaded inner surface 48, a twist lock connector, or any type of connector that provides a positive locking mechanism for connecting the endotracheal tube 26 to an oxygen or anesthetic gas supply means. The adapter handle 22 is configured to cooperate with whatever configuration is used for the first mounting element 34.

Referring to FIG. 2, the viewing assembly 24 of the preferred embodiment includes the shaft 28 having a distal end 56 and a proximal end 58. The shaft 28 carries a viewing conduit 54 for carrying an image through the shaft 28 from the distal end 56 to the proximal end 58 and further through a coupling 60 on the viewing conduit 54. The coupling 60 allows the viewing assembly 24 to be connected to an image viewing apparatus 62 so that the image can be displayed and viewed by the user of the invention. In the preferred embodiment, the coupling 60 is a spring-loaded, twist-lock, male, optical connector.

The shaft 28 of the viewing assembly 24 is preferably malleable so that the practitioner can bend the shaft 28 into a desired shape for a particular patient. The malleable shaft 28 of this embodiment substantially retains the shape into which it is bent while the breathing tube is being inserted into the patient. This feature allows the viewing system 20 to be used with endotracheal tubes 26 of any length for different size patients. Since the shaft 28 may be shaped as desired, a single standard length shaft 28 may be used for any patient. Preferably, the length of the shaft 28 is approximately as long as the longest available endotracheal tube 26.

In an alternate embodiment, however, the shaft 28 need not be malleable. Other intubation assist devices in the prior art commonly known as laryngoscopes are not malleable. These laryngoscopes form a passageway past the patient's tongue and teeth so that the endotracheal tube 26 can be inserted into the trachea. In alternate embodiment of the present invention, the shaft 28 can be rigid and can also be curved with the adapter handle 22 adapted to accommodate the particular shape of the rigid shaft 28.

In another embodiment, the shaft 28 is tubular so that the viewing conduit 54 may be carried within the tubular shaft 28. The tubular shaft 28 can also be malleable. The embodiment of the shaft 28 need not have a circular cross-section.

Yet another embodiment of the shaft 28 has an atraumatic tip of the type disclosed in U.S. Pat. No. 5,512,034. The bulbous tip prevents trauma to the patient should the shaft 28 of the viewing assembly 24 contact any internal tissue of the patient during the intubation procedure.

In the preferred embodiment as shown in FIGS. 1 and 2, the shaft 28 is tubular and malleable and the viewing conduit 54 is carried within the shaft 28. The preferred embodiment of the viewing assembly 24 also includes a handle portion 64 at the proximal end 58 of the shaft 28 where the viewing conduit 54 exits the shaft 28. The handle portion 64 can be molded around the proximal end 58 of the shaft 28 to provide a strain relief for the viewing conduit 54 and also to provide a gripping surface for the viewing assembly 24.

An example of the preferred embodiment of the viewing assembly 24 is the Clarus Model 2127 fiber-optic laryngoscope. The shaft 28 is approximately 38 cm in length, about 3.5 mm in diameter, and made of soft aluminum about 0.5 mm thick or annealed stainless steel about 0.3 mm thick.

The viewing conduit 54 of the preferred embodiment is at least one optic fiber 66 and preferably is a fiber-optic bundle 68. Multiple optic fibers 66 may be used to provide better image resolution or to carry illumination in addition to carrying an image. For example, the fiber-optic bundle 68 may be comprised of 30,000 fibers 66 each about 0.004 mm in diameter. The fibers 66 can be made of glass. An image focusing device 70 such as a lens may be associated with the fiber-optic bundle 68 at the distal end 56 of the shaft 28. Alternatively, the viewing conduit 54 can be any other suitable system which is flexible or bendable. A separate conduit 72 may be included to carry fluid to the distal end 56 of the shaft 28 in order to flush away debris or blood that may accumulate on the image focusing device 70 and obscure the image.

In the embodiment shown in FIGS. 6–9, the adapter handle 22 comprises a second mounting element 74 which is adapted to cooperate with the first mounting element 34 such that the adapter handle 22 receives and holds the shaft 28 in place within the lumen 36 of the endotracheal tube 26 when the first and second mounting elements 34 and 74 are operably associated. The first and second mounting elements 34 and 74 become operably associated when the second mounting element 74 is inserted into the cavity 44 of the first mounting element 34. The first mounting element 34 slips tightly over the second mounting element 74 while compressing the second mounting element 74 to hold the shaft 28.

The second mounting element 74 comprises a locking section 76. The locking section 76 is dimensioned to mate within the cavity 44 of the first mounting element 34. The locking section 76 of the preferred embodiment has the shape of a tapered cylinder. The diameter of the tapered locking section 76 is dimensioned so that as the locking section 76 is pushed into the cavity 44 of the first mounting element 34, an interference fit is eventually produced between the first and second mounting elements 34 and 74 when the locking section 76 is mounted within the cavity 44. The interference fit produces friction which holds the locking section 76 within the cavity 44 and also causes the locking section 76 to compress on the shaft 28 to hold it in place.

Once the adapter handle 22 and the viewing assembly 24 are mounted onto the endotracheal tube 26, the adapter handle 22 can be used as a handle to physically maneuver the endotracheal tube 26 past the patient's teeth, tongue, epiglottis, and vocal cords into its proper position about 2 to 4 cm (about 1 to 2 inches) in front of the bifurcation of the trachea.

Figure 10:
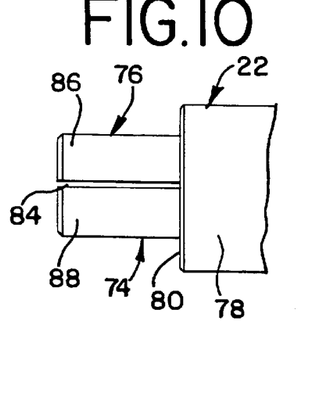
FIG. 10 is an enlarged, partial side elevational view of an alternate embodiment of the adapter handle.

In another embodiment, the locking section 76 is substantially cylindrical, as shown in FIG. 10, while the inner surface 48 defining the cavity 44 is tapered, as shown in FIG. 5. The same result of an interference fit will be obtained. Other possible embodiments of the locking section 76 may include non-cylindrically shaped locking sections 76 and cavities, i.e., rectangular or triangular, or threaded or snap-fit locking sections 76 which provide a positive mechanical connection between the first and second mounting elements 34 and 74.

In the preferred embodiment shown in FIGS. 6–9, the adapter handle 22 further comprises an elongated hollow body 78 having two ends 80 and defining a channel 82 between the ends 80 for movably receiving the shaft 28 when the adapter handle 22 is unmounted. Preferably, the adapter handle 22 holds the shaft 28 in place inside of the endotracheal tube 26 when the first and second mounting elements 34 and 74 are operably associated. The channel 82 is dimensioned to be larger in diameter than the shaft 28 so that the shaft 28 moves freely within the adapter handle 22 when the adapter handle 22 is not mounted within the cavity 44 of the first mounting element 34. The locking section 76 is disposed at one end of the hollow body 78.

The shaft 28 gripping feature of the second mounting element 74 may be accomplished in the preferred embodiment by a longitudinal slot 84 defined by the elongated hollow body 78. The longitudinal slot 84 is located at the end of the hollow body 78 that includes the locking section 76. The slot 84 extends radially from the channel 82 of the hollow body 78 and axially through the second mounting element 74. The slot 84 separates the second mounting element 74 into a first half 86 and a second half 88. When the adapter handle 22 is mounted in the cavity 44, the first mounting element 34 compresses the locking section 76, thereby squeezing together the first and second halves 86 and 88 of the locking section 76 which are separated by the slot 84. The squeezing together of the two halves 86 and 88 cause the halves 86 and 88 to compress on the shaft 28 which is in position within the channel 82 of the adapter handle 22.

Figure 11:
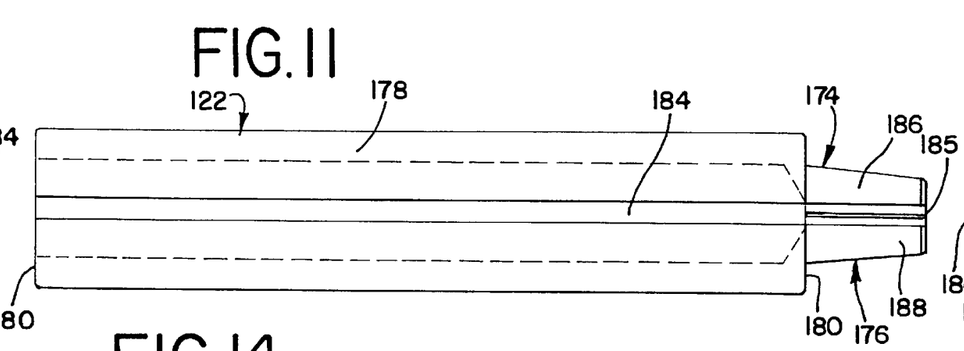
FIG. 11 is a side elevational view of an alternate embodiment of the adapter handle.
Figure 12:
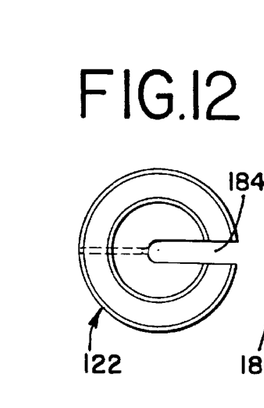
FIG. 12 is a rear elevational view of an alternate embodiment of the adapter handle.
Figure 13:
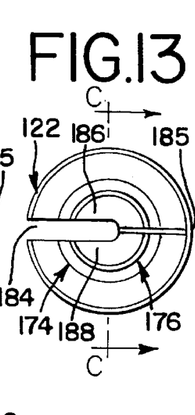
FIG. 13 is a front elevational view of an alternate embodiment of the adapter handle.

FIGS. 11–14 show an alternate preferred embodiment of the adapter handle 122. This embodiment is similar to the embodiment shown in FIGS. 6–9 except that the hollow body 178 and the second mounting element 174 define a substantially longitudinal shaft receiving slot 184 for receiving the shaft 28 of the viewing assembly 24. The slot 184 of this alternate embodiment extends radially from the axis of the elongated hollow body 178 as is shown in FIGS. 11–13. The slot 184 is for laterally receiving the shaft 28 of the viewing assembly 24 so that the adapter handle 122 may be assembled to the viewing assembly 24 by aligning shaft 28 with the slot 184 and inserting the shaft 28 into the adapter handle 122.

Additionally, the alternate embodiment of FIGS. 11–14 shows a clamping slot 185 defined by the second mounting element 174. The clamping slot 185 extends radially from the axis of the second mounting element 174 and extends axially through the second mounting element 174. The clamping slot 185 and the shaft receiving slot 184 are operably associated such that the second mounting element 174 grips and holds the shaft 28 in place within the lumen 36 of the endotracheal tube 26 via the same mechanism as the previously described preferred embodiment.

Figures 14, 15, 16:
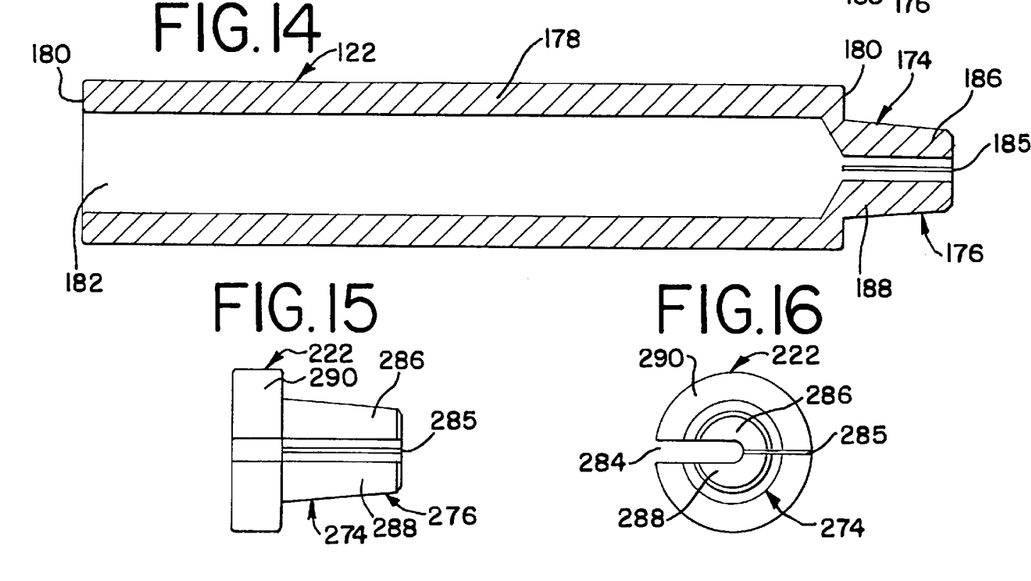
FIG. 14 is a cross-sectional view of an alternate embodiment of the adapter handle taken along plane C—C of FIG. 13.
FIG. 15 is a side elevational view of an alternate embodiment of the adapter handle.
FIG. 16 is a front elevational view of an alternate embodiment of the adapter handle.

FIGS. 15 and 16 show another alternate preferred embodiment of the adapter handle 222. This alternate embodiment comprises a second mounting element 274 which is similar in configuration to the second mounting elements of the previously described preferred embodiments. This embodiment also comprises a collar 290 extending radially from the second mounting element 222. The collar 290 of this embodiment takes the place of the elongated hollow body 78 and 178 of the previous embodiments. In this preferred embodiment, the collar 290 is disc shaped. The second mounting element 274 and the collar 290 define a shaft receiving slot 284 extending radially from the axis of the adapter handle 222. The second mounting element 274 also defines a clamping slot 285 which extends radially and axially through the second mounting element 274. The clamping slot 285 is operably associated with the shaft receiving slot 284 such that the adapter handle 222 grips and holds the shaft 28 in place within the lumen 36 of the endotracheal tube 28 when the second mounting element 274 is operably associated with the first mounting element 34.

In use, the alternate preferred embodiments of the adapter handle 122 and 222 shown in FIGS. 11–16 accomplish the same result of gripping and holding the shaft 28 within the lumen 36 of the endotracheal tube 26 by receiving the shaft 28 laterally through the shaft receiving slots 184 and 284.

The adapter handle 22 preferably is made of sterilizable plastic and is a simple, inexpensive, one-piece construction. The adapter handle 22 can be made by any method of manufacture suitable for making plastic pieces including injection molding or machining.

In use, the practitioner assembles the viewing system 20 by inserting the shaft 28 of the viewing assembly 24 into the adapter handle 22 and through the endotracheal tube 26. If the shaft 28 is malleable, it may first be shaped as desired or required for a particular patient. Alternatively, the shaft 28 may by shaped after the tube 26 is mounted onto the adapter handle 22.

Since endotracheal tubes 26 vary in length, the location of the viewing assembly 24 with respect to the end of the endotracheal tube 26 should preferably be adjustable. The present invention allows the user to align the distal end 56 of the shaft 28 of the viewing assembly 24 with respect to the distal end 32 of the tube 26, regardless of the length of the tube 26. Once the viewing assembly 24 is aligned, the adapter handle 22 with the viewing assembly 24 is mounted to the endotracheal tube 26 by mating the first and second mounting elements 34 and 74.

When mounted to the tube 26, the adapter handle 22 preferably compresses on the shaft 28 of the viewing assembly 24 to hold it in the desired position within the endotracheal tube 26. The adjustability provided by the adapter handle 22 is advantageous, because the end of the shaft 28 of the viewing assembly 24 can be placed substantially conterminously with the end of the endotracheal tube 26. This is desirable, because the viewing system 20 can provide an image of the tracheal area from the point of view of the end of the endotracheal tube 26.

After assembling the viewing system 20 and the endotracheal tube 26 and preparing the patient for intubation, the practitioner uses the image provided by the viewing system 20 as a guide to insert the endotracheal tube 26 into the trachea of the patient. The adapter handle 22 may be used together with the shaft 28 as a handle to maneuver the endotracheal tube 26 into position.

When the viewing assembly 24 and endotracheal tube 26 are successfully guided to the desired position within the trachea, the adapter handle 22 is disengaged from the endotracheal tube 26, and the viewing assembly 24 is removed while the tube 26 is held in place. The cuff 38 is then inflated and oxygen or other gases can be supplied to the patient.

Figure 17:
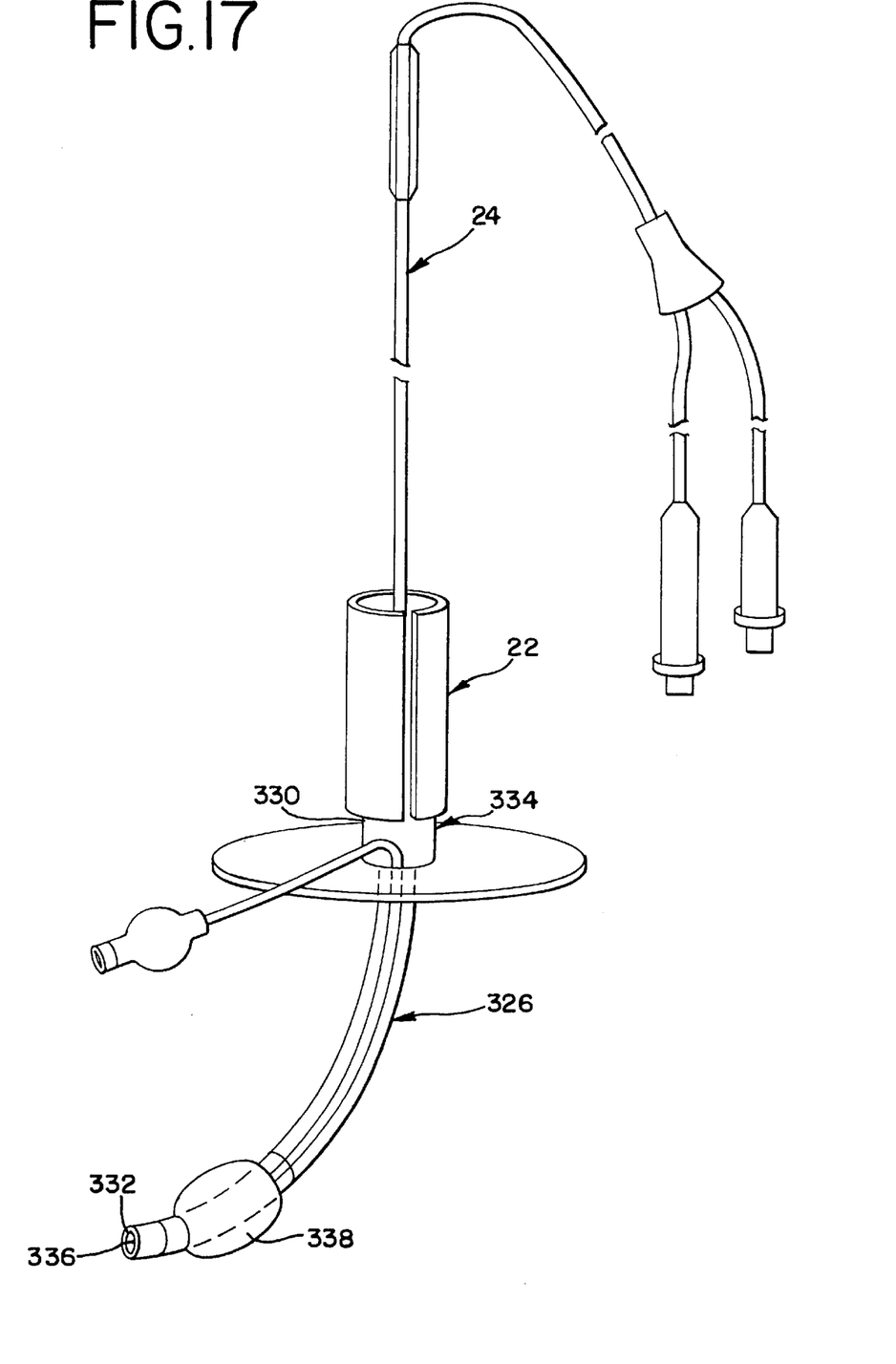
FIG. 17 is a perspective view showing the viewing system with the adapter handle and viewing assembly mounted onto a tracheostomy tube.

As shown in FIG. 17, the adapter handle 22, or any of its alternate embodiments, may be used with the viewing assembly 24 and a tracheostomy tube 326 in the same manner as with the endotracheal tube 26 as described herein. The tracheostomy tube 326 is inserted into the patient via an incision at the base of the patient's neck above the sternum. The tracheostomy tube 326 may have the same type of first mounting element 334 as the endotracheal tube 26. The tracheostomy tube 326 also has a proximal end 330, a distal end 332, a lumen 336, and an inflatable cuff 338.

Although the prior art has been described with reference to certain preferred embodiments, numerous modifications and variations can be made by those skilled in the art without departing from the novel spirit and scope of this invention.

What is claimed is:

1. A viewing system for use with a breathing tube; the breathing tube having a proximal end, a distal end, defining a lumen between the ends, and having a first mounting element on the proximal end; the viewing system comprising:

(a) a viewing assembly including a shaft having a proximal end and a distal end, and a viewing conduit carried by the shaft with a coupling on the conduit for connecting the conduit to an image viewing apparatus; and (b) an adapter handle having a second mounting element adapted to cooperate with the first breathing tube mounting element such that the adapter handle movably receives the shaft when the first and second mounting elements are not associated and holds the shaft in place where it has been moved within the lumen of the breathing tube when the first and second mounting elements are operably associated.

2. The viewing system of claim 1 wherein the adapter handle further comprises an elongated hollow body having two ends and defining a channel between the ends for movably receiving the shaft when the adapter handle is unmounted, and holding the shaft in place inside of the breathing tube when the first and second mounting elements are operably associated.

3. The viewing system of claim 2 wherein the elongated hollow body defines a substantially longitudinal slot having a predetermined width and extending radially from the channel and axially through the second mounting element such that the slot becomes narrower when the first mounting element cooperates with the second mounting element so that the shaft is held in place within the breathing tube.

4. The viewing system of claim 2 wherein the adapter handle defines an axis and the elongated hollow body defines a substantially longitudinal shaft receiving slot extending radially from the axis and axially through the elongated hollow body and through the second mounting element, and wherein the second mounting element defines a clamping slot extending radially from the axis and axially through the second mounting element.

5. The viewing system of claim 1 wherein the shaft is malleable such that it substantially retains its shape to which it is bent.

6. The viewing system of claim 1 wherein the shaft is tubular, and the viewing conduit is carried within the shaft.

7. The viewing system of claim 6 wherein the viewing conduit is a fiber-optic bundle.

8. A viewing system for use with a breathing tube; the breathing tube having a proximal end, a distal end, defining a lumen between the ends, and having a first mounting element on the proximal end; the viewing system comprising:
   (a) a viewing assembly including a shaft having a proximal end and a distal end, and a viewing conduit carried by the shaft with a coupling on the conduit for connecting the conduit to an image viewing apparatus;
   (b) an adapter handle having a second mounting element adapted to cooperate with the breathing tube first mounting element such that the adapter handle movably receives the shaft when the first and second mounting elements are not associated and holds the shaft in place within the lumen of the breathing tube when the first and second mounting elements are operably associated;
      the adapter handle further having an elongated hollow body having two ends and defining a channel between the ends for movably receiving the shaft when the adapter handle is unmounted, and holding the shaft in place inside of the breathing tube when the first and second mounting elements are operably associated; and
      the second mounting element including a locking section at one end of the elongated hollow body adapted to cooperate with the first mounting element, and the first mounting element including a hollow cylinder having an inner surface defining a cavity dimensioned such that an interference fit is produced between the first and second mounting elements when the locking section is mounted within the cavity.

9. The viewing system of claim 8 wherein the locking section is tapered and the inner surface defining the cavity is substantially cylindrical.

10. The viewing system of claim 8 wherein the locking section is substantially cylindrical and the inner surface defining the cavity is tapered.

11. A viewing system for use with a breathing tube; the breathing tube having a proximal end, a distal end, defining a lumen between the ends, and having a first mounting element on the proximal end; the viewing system comprising:
   (a) a viewing assembly including a malleable shaft having a proximal end, a distal end, and a length such that the malleable shaft is longer than the breathing tube; and a viewing conduit having a fiber-optic bundle carried by the malleable shaft with a coupling on the viewing conduit for connecting the viewing conduit to an image viewing apparatus; and
   (b) an adapter handle having an elongated hollow body with two ends, defining a channel between the ends for movably receiving the shaft, and having a second mounting element on one end of the elongated hollow body for slidably receiving and holding the malleable shaft at a desired location in place within the lumen of the breathing tube when the breathing tube first and mounting element second mounting element are operably associated.

12. The viewing system of claim 11 wherein the shaft is tubular, and the viewing conduit is carried within the shaft.

13. The viewing system of claim 11 wherein the adapter handle defines an axis and the elongated hollow body defines a substantially longitudinal shaft receiving slot extending radially from the axis and axially through the elongated hollow body and through the second mounting element, and wherein the second mounting element defines a clamping slot extending radially from the axis and axially through the second mounting element.

14. A viewing system for use with a breathing tube; the breathing tube having a proximal end, a distal end, defining a lumen between the ends, and having a first mounting element on the proximal end; the viewing system comprising:
   (a) a viewing assembly including a malleable shaft having a proximal end, a distal end, and a length such that the malleable shaft is longer than the breathing tube; and a viewing conduit having a fiber-optic bundle carried by the malleable shaft with a coupling on the viewing conduit for connecting the viewing conduit to an image viewing apparatus;
   (b) an adapter handle having an elongated hollow body with two ends, defining a channel between the ends for movably receiving the shaft, and having a second mounting element on one end of the elongated hollow body for receiving and holding the malleable shaft in place within the lumen of the breathing tube when the breathing tube first mounting element and second mounting element are operably associated; and
      the second mounting element including a locking section at one end of the elongated hollow body adapted to cooperate with the first mounting element, and the first mounting element including a hollow cylinder having an inner surface defining a cavity dimensioned such that an interference fit is produced between the first and second mounting elements when the locking section is mounted within the cavity.

15. The viewing system of claim 14 wherein the locking section is tapered and the inner surface defining the cavity is substantially cylindrical.

16. The viewing system of claim 14 wherein the locking section is substantially cylindrical and the inner surface defining the cavity is tapered.

17. A viewing system for use with a breathing tube; the breathing tube having a proximal end, a distal end, defining a lumen between the ends, and having a first mounting element on the proximal end; the viewing system comprising:
(a) a viewing assembly including a malleable shaft having a proximal end, a distal end, and a length such that the malleable shaft is longer than the breathing tube; and a viewing conduit having a fiber-optic bundle carried by the malleable shaft with a coupling on the viewing conduit for connecting the viewing conduit to an image viewing apparatus;
(b) an adapter handle having an elongated hollow body with two ends, defining a channel between the ends for movably receiving the shaft, and having a second mounting element on one end of the elongated hollow body for receiving and holding the malleable shaft in place within the lumen of the breathing tube when the breathing tube first mounting element and second mounting element are operably associated; and
the elongated hollow body defining a substantially longitudinal slot having a predetermined width and extending radially from the channel and axially through the second mounting element such that the second mounting element is divided into two halves, and the first mounting element cooperates with the second mounting element creating an interference fit between the first and second mounting elements causing the slot to become narrower such that the two halves of the second mounting element squeeze the malleable shaft and hold the malleable shaft in place within the breathing tube.

18. A viewing system for use with a breathing tube; the breathing tube having a proximal end, a distal end, defining a lumen between the ends, and having a first mounting element on the proximal end; the viewing system comprising:
(a) a viewing assembly including a shaft having a proximal end and a distal end, and a viewing conduit carried by the shaft with a coupling on the conduit for connecting the conduit to an image viewing apparatus;
(b) an adapter handle having a second mounting element adapted to cooperate with the breathing tube first mounting element such that the adapter handle movably receives the shaft when the first and second mounting elements are not associated and holds the shaft in place within the lumen of the breathing tube when the first and second mounting elements are operably associated; and
the adapter handle including a collar extending radially from the second mounting element, the adapter handle defining an axis, a substantially longitudinal shaft receiving slot extending radially from the axis and axially through the adapter handle, and a substantially longitudinal clamping slot extending radially from the axis and axially through the second mounting element, such that the clamping slot is operably associated with the shaft receiving slot.

19. A viewing system for use with a tube for insertion into a cavity of a body; the tube having a proximal end, a distal end, defining a lumen between the ends, and having a first mounting element on the proximal end; the viewing system comprising:
(a) a viewing assembly including a malleable shaft having a proximal end, a distal end, and a length such that the malleable shaft is longer than the tube; and a viewing conduit having a fiber-optic bundle carried by the malleable shaft with a coupling on the viewing conduit for connecting the viewing conduit to an image viewing apparatus; and
(b) an adapter handle having an elongated hollow body with two ends, defining a channel between the ends for movably receiving the shaft, and having a second mounting element on one end of the elongated hollow body for receiving and holding the malleable shaft in place at a desired location within the lumen of the tube when the breathing tube first mounting element and second mounting element are operably associated.

20. The viewing system of claim 19 wherein the shaft is tubular, and the viewing conduit is carried within the shaft.

21. The viewing system of claim 19 wherein the adapter handle defines an axis and the elongated hollow body defines a substantially longitudinal shaft receiving slot extending radially from the axis and axially through the elongated hollow body and through the second mounting element, and wherein the second mounting element defines a clamping slot extending radially from the axis and axially through the second mounting element.

22. A viewing system for use with a tube for insertion into a cavity of a body; the tube having a proximal end, a distal end, defining a lumen between the ends, and having a first mounting element on the proximal end; the viewing system comprising:
(a) a viewing assembly including a malleable shaft having a proximal end, a distal end, and a length such that the malleable shaft is longer than the tube; and a viewing conduit having a fiber-optic bundle carried by the malleable shaft with a coupling on the viewing conduit for connecting the viewing conduit to an image viewing apparatus;
(b) an adapter handle having an elongated hollow body with two ends, defining a channel between the ends for movably receiving the shaft, and having a second mounting element on one end of the elongated hollow body for receiving and holding the malleable shaft in place within the lumen of the tube when the breathing tube first mounting element and second mounting element are operably associated, and
the second mounting element including a locking section at one end of the elongated hollow body adapted to cooperate with the first mounting element, and the first mounting element including a hollow cylinder having an inner surface defining a cavity dimensioned such that an interference fit is produced between the first and second mounting elements when the locking section is mounted within the cavity.

23. The viewing system of claim 22 wherein the locking section is tapered and the inner surface defining the cavity is substantially cylindrical.

24. The viewing system of claim 22 wherein the locking section is substantially cylindrical and the inner surface defining the cavity is tapered.

25. A viewing system for use with a tube for insertion into a cavity of a body; the tube having a proximal end, a distal end, defining a lumen between the ends, and having a first mounting element on the proximal end: the viewing system comprising:
(a) a viewing assembly including a malleable shaft having a proximal end, a distal end, and a length such that the malleable shaft is longer than the tube; and a viewing conduit having a fiber-optic bundle carried by the malleable shaft with a coupling on the viewing conduit for connecting the viewing conduit to an image viewing apparatus;

(b) an adapter handle having an elongated hollow body with two ends, defining a channel between the ends for movably receiving the shaft, and having a second mounting element on one end of the elongated hollow body for receiving and holding the malleable shaft in place within the lumen of the tube when the breathing tube first mounting element and second mounting element are operably associated; and the elongated hollow body defining a substantially longitudinal slot having a predetermined width and extending radially from the channel and axially through the second mounting element such that the second mounting element is divided into two halves, the first mounting element cooperating with the second mounting element creating an interference fit between the first and second mounting elements causing the slot to become narrower such that the two halves of the second mounting element squeeze the malleable shaft and hold the malleable shaft in place within the tube.

26. A method for assembling a viewing system and a breathing tube; the breathing tube having a proximal end, a distal end, defining a lumen between the ends, and having a first mounting element on the proximal end; the method comprising:

(a) providing a viewing assembly including a shaft having a proximal end and a distal end, and a viewing conduit carried by the shaft with a coupling on the viewing conduit for connecting the viewing conduit to an image viewing apparatus;

(b) sliding an adapter handle onto the shaft, the adapter handle comprising a second mounting element for matingly cooperating with the breathing tube first mounting element;

(c) inserting the distal end of the shaft into the proximal end of the breathing tube and through the lumen;

(d) aligning the distal end of the shaft at a desired location with respect to the distal end of the breathing tube; and (e) mating the breathing tube first mounting element and second mounting element so that the shaft is fixed in position at the desired location within the lumen of the breathing tube.

27. The method of claim 26, including providing the viewing assembly wherein the shaft is malleable.

28. The method of claim 27, further comprising bending the shaft into shape.

29. The method of claim 26, including providing the viewing assembly wherein the viewing conduit has at least one optical fiber.

30. The method of claim 26, including providing the viewing assembly wherein the shaft is tubular.

31. The method of claim 30, including providing the viewing assembly wherein the viewing conduit is carried within the shaft.

32. The method of claim 31, including providing the viewing assembly wherein the viewing conduit has at least one optical fiber.

33. The method of claim 26, including providing the adapter handle further comprising an elongated hollow body having two ends and defining a channel between the ends for movably receiving the shaft when the adapter handle is unmounted and for gripping the shaft when the first and second mating elements cooperate.

34. The method of claim 33, including providing the adapter handle defining an axis and the elongated hollow body defining a substantially longitudinal shaft receiving slot extending radially from the axis and axially through the elongated hollow body and through the second mounting element, and wherein the second mounting element defines a clamping slot extending radially from the axis and axially through the second mounting element.

35. The method of claim 26 including providing the adapter handle further comprising a collar extending radially from the second mounting element, and wherein the adapter handle defines an axis, a substantially longitudinal shaft receiving slot extending radially from the axis and axially through the adapter handle, and a substantially longitudinal clamping slot extending radially from the axis and axially through the second mounting element, such that the clamping slot is operably associated with the shaft receiving slot.

36. A method for inserting a breathing tube into the trachea of a patient; the breathing tube having a proximal end, a distal end, defining a lumen between the ends, and a having first mounting element on the proximal end; the method comprising:

(a) providing a viewing assembly including a malleable shaft having a proximal end and a distal end, and a viewing conduit carried by the malleable shaft with a coupling on the viewing conduit for connecting the viewing conduit to an image viewing apparatus;

(b) sliding an adapter handle onto the malleable shaft, the adapter handle comprising a second mounting element for matingly cooperating with the breathing tube first mounting element;

(c) inserting the distal end of the malleable shaft into the proximal end of the breathing tube and through the lumen;

(d) aligning the distal end of the malleable shaft at a desired location with respect to the distal end of the breathing tube;

(e) mating the breathing tube first mounting element and second mounting element so that the malleable shaft is fixed at the desired location in position within the lumen of the breathing tube;

(f) bending the malleable shaft into a desired shape for insertion into the trachea of a patient;

(g) using the image provided by the viewing system as a guide; and (h) inserting the breathing tube into the trachea of the patient by using the adapter handle as a handle and the malleable shaft as support for manipulating the breathing tube.

37. The method of claim 36, including providing the viewing assembly wherein the viewing conduit has at least one optical fiber.

38. The method of claim 36, including providing the viewing assembly wherein the shaft is tubular.

39. The method of claim 38, including providing the viewing assembly wherein the viewing conduit is carried within the shaft.

40. The method of claim 39, including providing the viewing assembly wherein the viewing conduit has at least one optical fiber.

41. The method of claim 36, including providing the adapter handle further comprising an elongated hollow body having two ends and defining a channel between the ends for movably receiving the shaft when the adapter handle is unmounted and for gripping the shaft when the first and second mating elements cooperate.

42. The method of claim 41, including providing the adapter handle defining an axis and the elongated hollow body defining a substantially longitudinal shaft receiving slot extending radially from the axis and axially through the elongated hollow body and through the second mounting element, and wherein the second mounting element defines a clamping slot extending radially from the axis and axially through the second mounting element.

43. The method of claim 36, including providing the adapter handle further comprising a collar extending radially from the second mounting element, and wherein the adapter handle defines an axis, a substantially longitudinal shaft receiving slot extending radially from the axis and axially through the adapter handle, and a substantially longitudinal clamping slot extending radially from the axis and axially through the second mounting element, such that the clamping slot is operably associated with the shaft receiving slot.

* * * * *